United States Patent [19]

Konnerth

[11] 4,179,916

[45] Dec. 25, 1979

[54] METHOD OF AND A DEVICE FOR MEASURING THE PRESSURE AND ABRASION SENSITIVITY OF GRANULAR MATERIAL (GRAIN LOTS) DUE TO MECHANICAL STRESS

[76] Inventor: Wilhelm Konnerth, Otto-Flake-Str. 22, D-7570 Baden-Baden, Fed. Rep. of Germany

[21] Appl. No.: 868,910

[22] Filed: Jan. 12, 1978

[30] Foreign Application Priority Data

Jan. 13, 1977 [DE] Fed. Rep. of Germany ....... 2701152

[51] Int. Cl.² .......................... G01N 3/30; G01N 3/56
[52] U.S. Cl. ........................................ 73/7; 73/432 R
[58] Field of Search .................... 73/7, 432 R, 432 PS

[56] References Cited

U.S. PATENT DOCUMENTS

| | | | |
|---|---|---|---|
| 3,142,180 | 7/1964 | Glezen et al. | 73/432 PS |
| 3,972,220 | 8/1976 | Moore | 73/7 |
| 3,973,196 | 8/1976 | Hogg | 73/432 PS X |
| 4,026,157 | 5/1977 | Goebbels | 73/432 PS |

FOREIGN PATENT DOCUMENTS 1256738 12/1971 United Kingdom .

OTHER PUBLICATIONS

Starovoit et al., "Fast Method of Determining Toughness of Porous Coke"; Industrial Laboratory Publ., vol. 41; No. 6; 6-1975; pp. 917–921.

Primary Examiner—John Petrakes
Attorney, Agent, or Firm—Oblon, Fisher, Spivak, McClelland & Maier

[57] ABSTRACT

A method of measuring the pressure and abrasion sensitivity of granular material is disclosed wherein the mechanical stress is produced by an abrupt exposure of the grains of a representative sample, in a closed mortar, to a gas-pressure wave of high kinetic energy.

28 Claims, 2 Drawing Figures

METHOD OF AND A DEVICE FOR MEASURING THE PRESSURE AND ABRASION SENSITIVITY OF GRANULAR MATERIAL (GRAIN LOTS) DUE TO MECHANICAL STRESS

BACKGROUND OF THE INVENTION

1. Field of the Invention

The present invention relates to testing of the pressure and abrasion sensitivity of granular materials; to this end several testing methods are known. For instance, dumping sensitivity tests have been developed in numerous modifications; however, the numerical values obtained in these tests can, in general, not be compared to each other (cf. v. Bogdandy, Engell: Die Reduktion der Eisenerze (Reduction of Iron Ores), 1967, edited by Verlag Stahleisen, pp. 400 et seq.).

2. Description of the Prior Art

In most cases, abrasion sensitivity is tested in drums; the percentage of a certain range of grain-size fractions, e.g. 0 to 0.5 mm, after the drum process is considered as the test value in these tests.

A method of this type, wherein the granular material is exposed to mechanical stress and wherein either the variation of the weight proportions of individual grain-size fractions due to this stress in comparison to the corresponding initial values of a representative sample, by way of screening analysis, or the variation of the permeability to gas of the processed sample in comparison to that of the non-processed sample is applied as a standard of pressure sensitivity and abrasion sensitivity, is known from German patent application No. 17,73,737 published for opposition.

The disclosure of German published patent application P 17,73,737 is incorporated herein by reference.

In the aforementioned methods, however, the test materials are tested only in the form of a loose bulk material whose grains still have a comparatively high freedom of relative movement during the test procedure. Hence, the results of such test procedures are practically irrelevant for a majority of industrial processing engineering, i.e. for those fields where grain lots in dense packing (i.e. with an intense mutual influence of the individual grains) plays a decisive role.

SUMMARY OF THE INVENTION

An object of the present invention is to provide a reliable test method to measure the pressure and abrasion sensitivity of densely packed granular material, which hence furnishes a numerical result which better reflects the actual conditions in practice.

A further object of the present invention is to provide a particularly suitable device to carry through this method.

In accordance with the inventive method the mechanical stress is produced by an abrupt exposure of the grains of the representative sample, in a closed mortar, to a gas-pressure wave of high kinetic energy.

In this method, all grains of the material of the lot are subjected, in dense lot formation, to pressure and abrasion forces. The magnitude of the mechanical stress to which the grain lot is exposed depends on the kinetic energy of the gas-pressure wave and can be controlled by the conditions of the test, e.g. the kind and quantity of the employed explosive agent and/or the quantity of the test material used as sample.

The test method can be applied to grain lots of materials of any kind when measured results of pressure and abrasion sensitivities are relevant.

There is practically no restriction, either in the positive or in the negative direction, relative to the admissible particle size of the test material.

A device to carry out this new method comprises either a screening analysis means or a device which is provided with means to establish the variation of permeability to gas, wherein the mortar comprises a main body and one or more cavities, and wherein the inner surface of one or several of the cavities differs from the remaining material of the mortar body as far as surface structure, material composition and/or physical and chemical properties are involved.

BRIEF DESCRIPTION OF THE DRAWINGS

Various other objects, features and attendant advantages of the present invention will be more fully appreciated as the same becomes better understood from the following detailed description when considered in connection with the accompanying drawings, wherein like reference characters designate like or corresponding parts throughout the several views, and wherein.

DETAILED DESCRIPTION OF THE PREFERRED EMBODIMENTS

Figure 1:
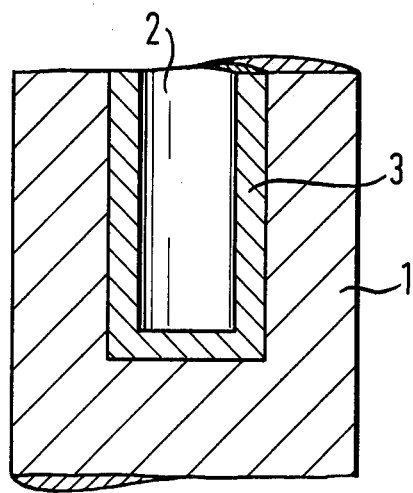
FIG. 1 illustrates a sectional view of a part of the mortar, being a part of the device of the present invention; and, FIG. 2 shows the complete test equipment comprising the present invention.

FIG. 1 illustrates that the mortar comprises a main body 1 and one or several cavities 2 with an equal or a different structure.

The individual cavity 2 can either be provided as a recess in the main body 1 or can be inserted into the main body 1 from outside as an independent hollow body 3 which is suitably anchored in the main body 1.

The mortar main body 1, the cavity walls and the hollow bodies 3 may be of different materials with the same or different surface properties.

The outside dimensions of the insertable hollow bodies 3 are equal to each other, irrespective of the size and the shape of the cavity 2 which they enclose, so that they can be mutually exchanged in the holders provided in the main body 1.

Each mortar cavity 2 and/or hollow body 3 is suitably designed with respect to its shape and volume so that it is adapted to the respective application of the mortar.

Figure 2:
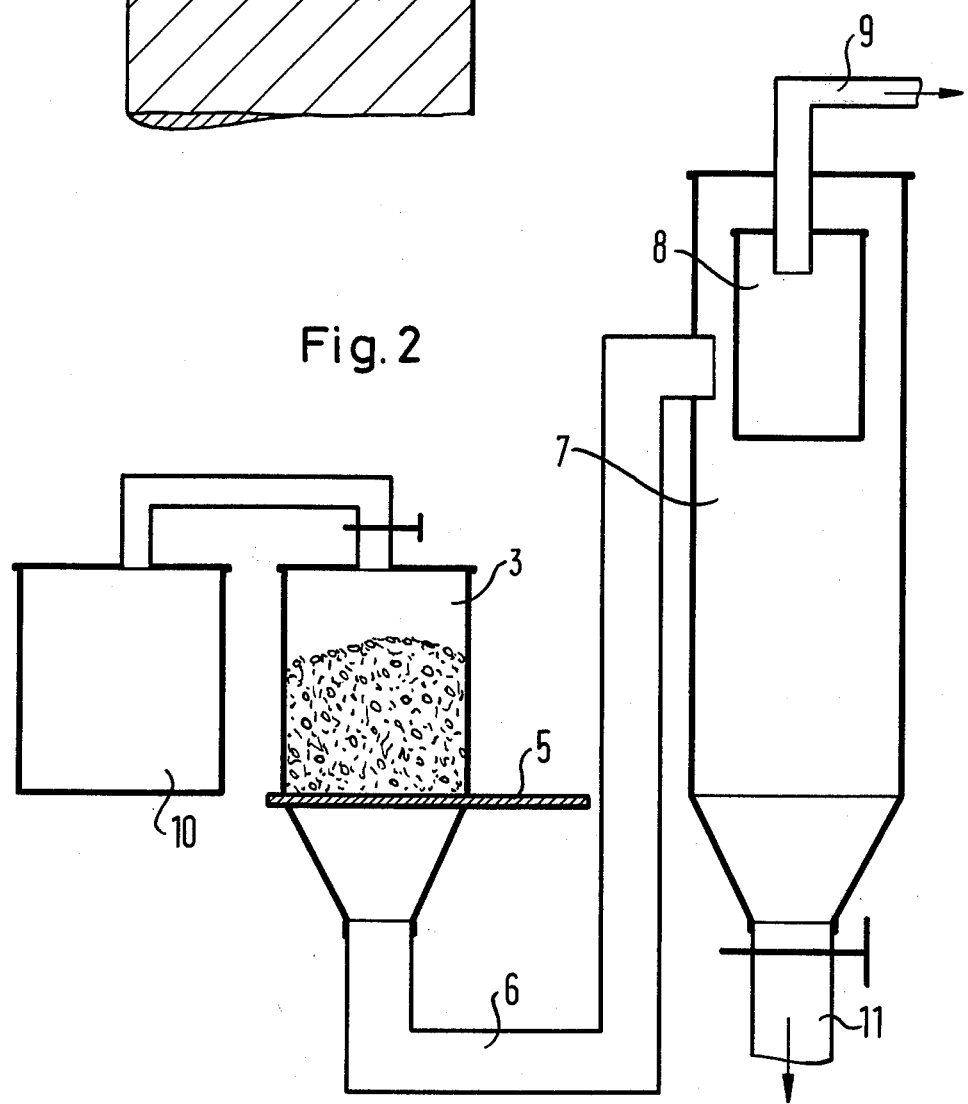

FIG. 2 shows one embodiment of the complete test equipment of the present invention, i.e. the mortar and means connected thereo at the inlet and the outlet sides. The grain lot, which is processed, for instance, by detonation of an explosive agent in one or several of the mortar cavities 2 and/or hollow bodies 3 of the mortar, is transferred through the line 6 to the filter chamber 7 with the aid of the produced pressurized gas, subsequently to opening of the closure 5; in the filter chamber 7 it is deposited at the filter 8. The dust-free gas is then transferred, if necessary through a gas washer (which is not illustrated), through line 9 to the open air. The pressure gas leaving the filter unit passes the washer before it reaches atmosphere. The type and amount of the washer liquid depends on the composition and amount of the gas to be washed and the respective legal regulations (for example, e.g. environmental protection, etc.). If the mortar is in an open air environment or in a laboratory under an exhaust or the pressure gas leaving the mortar does not represent a danger for the environment, no gas washer is thus required. However, it is also possible to produce additional pressurized gas in another cavity and/or hollow body 10 which do not contain test material, with the aid of a second explosive charge. The thus produced gas is then used, if necessary, either to flush the cavity 2 and/or the hollow body 3 a second time or to assist in the pneumatic transfer of the processed material to the filter chamber 7. The test material deposited there leaves the filter chamber through line 11 and arrives in the screening system (which is not illustrated).

It is possible, of course, to carry through tests with this mortar in a simpler way, e.g. in a manner such that the pressurized gas produced in the cavity 2 is allowed to escape slowly to the outside through one or several openings provided with filter inserts, whereupon, after opening of the closure 5, the processed grain lot is discharged by hand and then put into the screening set, or that the material is allowed to drop from the mortar into the screening set therebelow. In accordance with the object of the test, the position of the mortar axes in space can be suitably varied.

During processing of the test material in the mortar the mortar can be either in rest or moving. The explosive force which is exerted in the mortar on the test material has a wearing effect on the same with regard to pressure and friction. The size of the kinetic energy which must be exerted on the grain aggregate to be investigated depends upon the sensitivity of the material vis a vis mechanical wear.

Obviously, many modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of measuring the pressure and abrasion sensitivity of granular material in a closed mortar comprising exposing said material to a mechanical stress; and,
    comparing the variation of the weight proportions of the individual grain-size fractions of said granular material due to said stress in comparison to corresponding initial values of a representative sample of granular material, by screening analyses, including producing said mechanical stress by an abrupt exposure of the grains of said representative sample in said closed mortar to a gas-pressure wave of high kinetic energy.

2. A method as claimed in claim 1 further comprising producing said gas-pressure wave by an abrupt conversion of an explosive solid in said mortar.

3. A method as claimed in claim 1 further comprising controlling the magnitude of said mechanical stress by the lot quantity of said granular material.

4. A method as claimed in claim 1 further comprising pneumatically discharging said representative material sample from said mortar after exposure of the material grains to said gas-pressure wave by pressurized gas produced in said mortar.

5. A method as claimed in claim 4 further comprising passing said pressurized gas loaded with material grains through a filtering system, then a gas washer and only then releasing said pressurized gas to atmosphere.

6. A method as claimed in claim 5 further comprising transferring said granular material, after exposure to said pressure wave, from said mortar to said filtering system, through another gaseous medium.

7. A method as claimed in claim 5 further comprising transferring said granular material, after exposure to said pressure wave, from said mortar directly to a screening system through another gaseous medium.

8. A method as claimed in claim 4 further comprising passing said pressurized gas loaded with material grains through a filtering system and only subsequently releasing said pressurized gas to atmosphere.

9. A device for measuring pressure and abrasion sensitivity of granular material which comprises:
    means for applying stress to said material;
    screening analysis means for comparing the variation of the weight proportions of individual grain-size fractions of said material due to said stress in comparison to corresponding initial values of a representative sample; and
    a mortar including a main body and one or more cavities, wherein the inner surface of said one or more cavities differs from the remaining material of said mortar body with respect to surface structure, material composition and physical and chemical properties thereof.

10. A device as claimed in claim 9, wherein said cavities are each shaped like a hollow body of rotation.

11. A device as claimed in claim 9 wherein said one or more cavities are designed as independent hollow bodies inserted into and firmly anchored in recesses in said main body.

12. A device as claimed in claim 11, wherein independently of the shape and size of each of the respectively contained cavities, the outside dimensions of said hollow bodies are equal to each other so that said hollow bodies in said recesses of said mortar body are suited for optional mutual exchange.

13. A device as claimed in claim 11, wherein said main body and said hollow bodies are made of the same materials.

14. A device as claimed in claim 11, wherein said main body and said hollow bodies are made of different materials.

15. A method as claimed in claim 1 further comprising producing said gas-pressure wave by an abrupt conversion of an explosive liquid in said mortar.

16. A method as claimed in claim 1 further comprising producing said gas-pressure wave by an abrupt conversion of an explosive gaseous substance in said mortar.

17. A method as claimed in claim 1 further comprising controlling the magnitude of said mechanical stress by the lot quantity and the kind and quantity of the substance employed to produce said gas-pressure wave on said granular material.

18. A method as claimed in claim 1 further comprising controlling the magnitude of said mechanical stress by the kind and quantity of the substance employed to produce said gas-pressure wave on said granular material.

19. A method of measuring the pressure and abrasion sensitivity of granular material in a closed mortar comprising:
    exposing said material to mechanical stress; and, comparing the variation of the permeability to gas of the material exposed to mechanical stress to that of corresponding initial values of a representative sample as a standard of pressure sensitivity and abrasion sensitivity including producing said mechanical stress by an abrupt exposure of the grains of said representative sample in said closed mortar to a gas-pressure wave of high kinetic energy.

20. A method as claimed in claim 19 further comprising producing said gas-pressure wave by an abrupt conversion of an explosive solid in said mortar.

21. A method as claimed in claim 19 further comprising producing said gas-pressure wave by an abrupt conversion of an explosive liquid in said mortar.

22. A method as claimed in claim 19 further comprising producing said gas-pressure wave by an abrupt conversion of an explosive gaseous substance in said mortar.

23. A method as claimed in claim 19 further comprising controlling the magnitude of said mechanical stress by the lot quantity of said granular material.

24. A method as claimed in claim 19 further comprising controlling the magnitude of said mechanical stress by the lot quantity and the kind and quantity of the substance employed to produce said gas-pressure wave on said granular material.

25. A method as claimed in claim 19 further comprising controlling the magnitude of said mechanical stress by the kind and quantity of the substance employed to produce said gas-pressure wave on said granular material.

26. A method as claimed in claim 19 further comprising pneumatically discharging said representative material sample from said mortar after exposure of the material grains to said gas-pressure wave by pressurized gas produced in said mortar.

27. A method as claimed in claim 19 further comprising passing said pressurized gas loaded with material grains through a filtering system and releasing said pressurized gas to atmosphere.

28. A method as claimed in claim 27 further comprising transferring said granular material, after exposure to said pressure wave, from said mortar to said filtering system, through another gaseous medium.

* * * * *